United States Patent
Savidge et al.

(10) Patent No.: US 10,280,470 B2
(45) Date of Patent: May 7, 2019

(54) **BIOMARKERS OF RECURRENT *CLOSTRIDIUM DIFFICILE* INFECTION**

(71) Applicant: Baylor College of Medicine, Houston, TX (US)

(72) Inventors: Tor Savidge, League City, TX (US); Emily Hollister-Branton, Houston, TX (US)

(73) Assignee: Baylor College of Medicine, Houston, TX (US)

(*) Notice: Subject to any disclaimer, the term of this patent is extended or adjusted under 35 U.S.C. 154(b) by 146 days.

(21) Appl. No.: 14/759,918

(22) PCT Filed: Jan. 13, 2014

(86) PCT No.: PCT/US2014/011266
§ 371 (c)(1),
(2) Date: Jul. 8, 2015

(87) PCT Pub. No.: WO2014/110493
PCT Pub. Date: Jul. 17, 2014

(65) Prior Publication Data
US 2015/0344940 A1    Dec. 3, 2015

Related U.S. Application Data

(60) Provisional application No. 61/751,460, filed on Jan. 11, 2013.

(51) Int. Cl.
| | | |
|---|---|---|
| *C12Q 1/689* | (2018.01) | |
| *A61K 35/742* | (2015.01) | |
| *C12Q 1/6883* | (2018.01) | |

(52) U.S. Cl.
CPC ............ *C12Q 1/689* (2013.01); *A61K 35/742* (2013.01); *C12Q 1/6883* (2013.01)

(58) Field of Classification Search
CPC ..... C12Q 1/689; C12Q 1/6883; A61K 35/742
USPC ...................................................... 424/93.41
See application file for complete search history.

(56) References Cited

FOREIGN PATENT DOCUMENTS

| | | |
|---|---|---|
| WO | 2011146968 A1 | 12/2011 |
| WO | 2012142605 A1 | 10/2012 |
| WO | 2013070962 A1 | 5/2013 |

OTHER PUBLICATIONS

Chang et al., "Decreased Diversity of the Fecal Microbiome in Recurrent Clostridium difficile—Associated Diarrhea," The Journal of Infectious Diseases, Jan. 16, 2008 (Jan. 16, 2008), vol. 197, pp. 435-438.
Khoruts et al., "Changes in the Composition of the Human Fecal Microbiome After Bacteriotherapy for Recurrent Clostridium difficile-associated Diarrhea," Journal of Clinical Gastroenterology, May 1, 2010 (May 1, 2010). vol. 44, No. 5, pp. 354-360.
Plassart et al., "First case of intra-abdominal infection with Clostridium disporicum," Anaerobe, Dec. 12, 2012 (Dec. 12, 2012). vol. 19, pp. 77-78.
Louie et al., "OPT-80 Eliminates Clostridium difficile and is Sparing of Bacteroides Species during Treatment of C. difficile Infection," Antimicrobial Agents and Chemotherapy, Oct. 27, 2008 (Oct. 27, 2008), vol. 53, No. 1, pp. 261-263.
Hopkins et al., "Changes in predominant bacterial populations in human faeces with age and with Clostridium difficile infection" Journal of Medical Microbiology, May 1, 2002 (May 1, 2002), vol. 51, No. 5, pp. 448-454.
Theunissen et al., "Clostridium difficile colitis in cystic fibrosis patients with and without lung transplantation," Transplant Infectious Disease, Jul. 12, 2007 (Jul. 12, 2007). vol. 10, Iss. 4, pp. 240-244.
Antharam et al., "Intestinal Dysbiosis and Depletion of Butyrogenic Bacteria in Clostridium difficile Infection and Nosocomial Diarrhea," Journal of Clinical Microbiology, Jun. 26, 2013 (Jun. 26, 2013), vol. 51, No. 9, pp. 2884-2892.

*Primary Examiner* — Jennifer M. H. Tichy
(74) *Attorney, Agent, or Firm* — Norton Rose Fulbright US LLP

(57) ABSTRACT

Embodiments of the invention include methods and/or compositions for analysis of samples for *C. difficile* infection to determine whether or not an individual is at risk for having recurrent *C. difficile* infection or a CDI misdiagnosis. Methods include characterization of microflora composition from the gut, wherein alterations of the microflora gut composition are indicative of recurrence of infection. Methods include analysis of nucleic acids from the gut, such as 16S rRNA as being identifying of a particular bacteria in the analysis of bacterial populations of the gut.

13 Claims, 4 Drawing Sheets

BIOMARKERS OF RECURRENT *CLOSTRIDIUM DIFFICILE* INFECTION

CROSS-REFERENCE TO RELATED APPLICATIONS

The present application is a national phase application under 35 U.S.C. § 371 that claims priority to International Application No. PCT/US2014/011266 filed Jan. 13, 2014, which claims the benefit of priority to U.S. Provisional Application Ser. No. 61/751,460, filed Jan. 11, 2013, both applications are incorporated herein by reference in their entirety.

TECHNICAL FIELD

The fields of the invention include at least microbiology, bacteriology, medicine, diagnostics, cell biology, and molecular biology. In at least specific embodiments, the fields include treatment, diagnosis, prevention, and/or prognosis of *Clostridium* infection.

BACKGROUND OF THE INVENTION

The number of hospitalized patients with a *Clostridium difficile* infection (CDI) discharge diagnosis has increased dramatically due in part to the use of more sensitive methods involving nucleic acid amplification for diagnosis and to the emergence of epidemic strains, such as BI/NAP1/027 and 078. Vancomycin and Metronidazole have long been preferred treatment options in CDI, but neither is fully effective as evidenced by up to 35% clinical recurrence and significant fatality rates. Medical treatment and hospitalization associated with CDI burdens the U.S. health care system with up to $3.8 billion in excess costs each year, with much of the expense attributable to disease recurrence. Reduction in recurrence, therefore, is a priority clinical need and major market opportunity.

There is a need in the art to provide a comprehensive categorization of individuals based on molecular and/or phenotypic variables in light of the complex genetic, proteomic, and environmental interactions associated with CDI. There is a need in the art to characterize molecules (such as nucleic acids) from the samples of individuals using biomarkers of clinical genotype, phenotype, activity, and/or treatment. Current FDA-approved diagnostic assays for CDI are limited by their cost, technical complexity, long assay duration and/or sensitivity. No diagnostic assays currently exist that predict disease relapse in CDI, and these are urgently warranted, nor are there available any treatment therapies based on such diagnostic information.

BRIEF SUMMARY OF THE INVENTION

The present invention is directed to systems, methods, and/or compositions related to recurrent pathogenic infection, including recurrent bacterial infection, such as recurrent *Clostridium* infection. In specific embodiments, the present invention concerns systems, methods, and/or compositions related to primary and recurrent *Clostridium difficile* infection. The individual may be infected pathogenically with *Clostridium difficile* alone or in combination with other pathogenic organisms. Although the present disclosure describes embodiments for *C. difficile*, the presence or absence of any *Clostridium* species may be assayed with analogous methods to the disclosure.

In particular embodiments of the invention, there is a single or multi-faceted approach to characterizing gut-microbial ecology and mechanisms of recurrent *Clostridium difficile* infection. In specific embodiments, there is a multi-omics approach to characterizing the gut-microbial ecology and mechanisms of recurrent *Clostridium difficile* infection.

In specific embodiments, the invention encompasses treatment applications related to recurrent *Clostridium difficile* infection. In some embodiments, the invention encompasses diagnostic, preventative, and/or prognostic applications related to recurrent *Clostridium difficile* infection. In certain embodiments, the invention concerns treatment, prevention, diagnosis, and/or prognosis of epidemic strains of *Clostridium difficile* infection, an example of which is BI/NAP1/027 or 078. Other ribotypes that are encompassed as examples include at least 106, 001, 014, 020, 015, 002, 023, 015, and 016.

Embodiments of the disclosure provide methods of determining whether or not an individual that is suspected of having or at risk for having recurrent pathogenic *C. difficile* infection (CDI) will have the recurrent *C. difficile* infection. Results of methods of the disclosure may indicate that the individual in question has a pathogenic CDI or that the individual in question does not have a pathogenic CDI. An individual suspected of having CDI or at risk for having CDI may include those of increasing age (except for infancy), in addition to duration of antibiotic regimen, administration of particular or multiple antibiotics, severity of underlying diseases, non-surgical gastrointestinal procedures, presence of a nasogastric tube, medications for ulcers, depression and insomnia, intensive care unit admission, and duration of hospital stay.

In particular aspects, an individual is suspected of having recurrent CDI based on one or more symptoms of CDI, and as a result at least one sample from the individual is subjected to methods of the invention. The sample may be a stool or biopsy sample that may be obtained by any suitable method in the art. The sample contains a variety of bacterial cells with nucleic acid that is extracted from the cells, and the nucleic acid is analyzed for the content of their 16s rRNA (either in RNA or DNA form), for example. When the analysis of the 16srRNA indicates that the levels of one or more bacteria are present in elevated amounts or that the levels of one or more bacteria are present in reduced amounts, the individual is provided a particular treatment. The treatment may be treatment for pathogenic CDI, depending on the level of certain bacteria. The treatment may be treatment for disease other than pathogenic CDI, depending on the level of certain bacteria. In some cases, certain treatments are avoided based on the results of the methods of the disclosure.

In certain embodiments of the invention, there is analysis of a sample that indicates there is the presence of *C. difficile*, but further analysis is employed to clarify whether or not the particular *C. difficile* strain is pathogenic. Although any particular method in the art may be employed to identify a pathogenic strain, in certain cases a toxin analysis is performed. Toxins that may be assayed for include toxin A and/or toxin B, and binary toxin. Toxins are assayed to distinguish disease causing toxigenic *C. difficile* from non-toxigenic *C. difficile* both of which can form part of the commensal microbiota in approximately 5% of healthy subjects. Several assay methods are available to measure toxin types and include ELISA, PCR, isothermal amplification, cytotoxicity assay, and/or enzyme-linked cytotoxicity assay, for example.

In some cases, glutamate dehydrogenase (GDH) test detects an antigen that is produced in high amounts by *C. difficile*. Tissue culture to detect the *C. difficile* toxin is a test that looks for the effects of the cytotoxin on human cells grown in culture, and it may be employed. In specific embodiments, analysis of nucleic acid is employed to distinguish pathogenic strains from non-pathogenic strains; for example, one or more mutations or polymorphisms between strains of *C. difficile* may be the target of a nucleic acid assay, cytotoxicity assay, and/or bacterial culture assay.

The inventors have been able to successfully identify profiles (such as of nucleic acids) in clinical specimens that classify CDI with a high degree of confidence. Furthermore, the inventors have identified profiles in clinical stool specimens that identify susceptibility to disease recurrence. In one aspect a nucleic acid profile is derived from a sample, such as a stool sample. In certain aspects, the profile can be diagnostic or prognostic of a number of pathological conditions. In certain embodiments, a metabolic profile can identify a subject with CDI or who has or is at risk for recurrent CDI.

In a further aspect, subjects having a non-recurrent infection can be distinguished from subjects having or at risk of having a recurrent infection by assessing the levels of one or more particular bacteria.

In particular embodiments of the invention, one or more nucleic acids are assayed for in a sample from the individual. The nucleic acids specifically identify a particular bacterium, such as *C. difficile*. In specific embodiments, the nucleic acids are highly conserved within a species, including within *C. difficile*. In specific cases, the nucleic acids are 16S rRNA or DNA that encodes 16S rRNA.

In certain aspects, the levels of particular bacteria are elevated based on assaying for their respective 16S rRNA or DNA that encodes their respective 16S rRNA. In certain aspects, a more aggressive or targeted or prophylactic treatment is administered to those subjects identified as having or being at risk of recurrent infection. The term "elevated" refers to a statistically significant difference (e.g., an increase of at least 5%, 10%, 20%, 25%, 35%, 40%, 45%, 50%, 55%, 60%, 65%, 70%, 75%, 80%, 85%, 90%, 95%, 100%, 120%, 140%, 160%, 180%, 200%, 220%, 240%, 260%, 280%, or 300% increase or more) in a measured level compared to a reference level. The term "decreased" refers to a statistically significant difference (e.g., a decrease of at least 5%, 10%, 20%, 25%, 35%, 40%, 45%, 50%, 55%, 60%, 65%, 70%, 75%, 80%, 85%, 90%, 95%, 100%, 120%, 140%, 160%, 180%, 200%, 220%, 240%, 260%, 280%, or 300% decrease or more) in a determined or measured level compared to a reference level. The term "reference level" means a threshold level or a level in a control subject, a control population, or an average of control population, or a level previously measured in the same individual. A reference level will depend on the assay performed and can be determined by one of ordinary skill in the art. The reference level can be used to distinguish subjects having and not having a condition or disease, e.g., CDI.

In certain aspects a biological sample can be a stool, urine, or blood sample. In further aspects the biological sample is a stool or biopsysample. In still further aspects the stool or biopsy sample can be obtained from a subject having or has recently had diarrhea (within 1, 2, 3, 4, 5, 6, 7, 8, 9, 10, 11, 12, hours or days).

In certain aspects, methods are directed to the identification of accurate stool biomarkers for a gastrointestinal condition, e.g., CDI, and translation of these findings into effective diagnostic, prognostic, and/or nutraceutical therapies.

In some aspects, additional methods are utilized to facilitate analysis of whether or not an individual has CDI or will have an increased risk of disease relapse or recurrence of CDI. In some additional methods, assessment of disease progression and relapse is based on the concept that gut microbe composition is an important determinant in whether CDI patients are susceptible to relapse. In aspects, network and disease classification analysis of the stool metabolome has identified highly significant differences in biochemical profiles that enable positive-categorization of CDI patients from other cases of antibiotic-associated diarrhea with a high degree of confidence. Increases or decreases in metabolites related to bacterial activity and inflammation are evident in CDI patients, e.g., altered nitrogen metabolism, bile acid conjugation, and polyamine metabolism. The pathophysiological relevance of a metabolomics approach in CDI is supported by highly significant changes recorded in nitrogen-based metabolite and dietary cofactor regulators of *C. difficile* virulence.

Other aspects are directed to a method for identifying and/or selecting a prophylactic dietary supplement or prebiotic therapy for the treatment of microbial infections. In certain aspects methods of treating *C. difficile* infection comprises providing phytic acid supplements or stable phytic-acid derivatives.

In certain aspects, methods are directed to measurement of a stool metabolome of CDI patients to identify and predict patterns of disease progression and relapse.

In a further aspect, cross-validated out-of-sample error rate and bipartite network analysis of metabolomics data has demonstrated excellent disease classification for cytotoxicity-confirmed CDI. In certain aspects, the inventors can demonstrate the ability to predict symptomatic CDI with an accuracy of at least or about 76, 78, 80, 82, 84, 86, 88, 90, 92, 94, 96, 98, or 99%, including all values and ranges therebetween.

In certain aspects, assessment of the biomarkers described herein can provide an analysis with a misclassification rate of 24% between non-infected and CDI infected patients.

Analysis of recurrent versus non-recurrent CDI can be determined with a misclassification rate of 39%. Disease relapse within 6 weeks can be determined in 61% of patients at the time of original diagnosis.

In some embodiments of the invention, one or more additional methods other than analysis of nucleic acids (such as 16S rRNA) are employed for analysis of *C. difficile* infection. In some embodiments of the invention, one or more additional methods other than analysis of nucleic acids (such as 16S rRNA) are employed for analysis of likelihood of recurrence of *C. difficile* infection. In specific embodiments, one or more metabolites from a sample are analyzed to ascertain whether or not there is *C. difficile* infection or whether or not there is a susceptibility to recurrence of *C. difficile* infection. In specific embodiments, particular metabolites that may be measured include one or more biomarkers selected from 5-aminovalerate, N-acetylglutamate, thymine, agmatine, putrescine, gamma-aminobutyrate, (GABA), ammonia, X-16563, X-16071, X-15461, or X-15175, for example. The metabolites may be produced by one or more pathogenic bacteria in the individual and/or be a host response to one or more pathogenic bacteria in the individual.

In particular embodiments of the invention, an individual having diarrhea is tested for the presence of *C. difficile* (such as using toxin-based analyses and/or nucleic acid analysis). At that time, or at a later time, one may analyze the individual's sample using methods of the invention to predict recurrence of *C. difficile* infection and assist in determination of management, including using therapies that would only be necessary for recurrent *C. difficile* infection (to avoid excessive use of particular antibodies and/or contain costs (given that some may be expensive, such as fidaxomicin or antitoxin monoclonal antibody, for example)).

The individual or entity performing analysis of a sample of an individual may or may not be the same individual or entity that obtained the sample or that provided directly or indirectly a treatment regimen based on the analysis of the sample.

In some embodiments, there is a method for distinguishing an individual having or being at risk for recurrent *Clostridium* infection from an individual having non-recurrent *Clostridium* infection, comprising the step of analyzing nucleic acid in a gut sample from the individual, wherein the nucleic acid is indicative of the presence or level of one or more bacteria from a microflora population in the gut. In at least specific cases, the *Clostridium* is *Clostridium difficile*, *Clostridium perfingens*, *Clostridum botulinum*, or a mixture thereof. In particular embodiments, there is a shift, including a detectable shift by routine methods in the art, in the identity and/or level of one or more bacteria from the microflora population. In specific embodiments, the nucleic acid is analyzed by polymerase chain reaction, sequencing, isothermal amplification, bioinformatics (such as, for example, clustering of sequences into operational taxonomic units (OTUs) at a level of 97% similarity, and assigning identities to these OTUs using BLAST searches of 16S rRNA gene databases (specifically: NCBI nr and the Ribosomal Database Project 16S rRNA gene database)), or a combination thereof. In specific aspects, the nucleic acid encodes 16S rRNA or is reverse transcribed from 16S rRNA.

In some embodiments, methods of the invention comprise the step of analyzing the sample for one or more toxins from *Clostridium*. In some embodiments, methods of the invention comprise the step of analyzing the sample for one or more metabolites. In some aspects, the method further comprises the step of extracting DNA from the sample.

In some embodiments, one or more bacteria of the gut microflora are selected from the group consisting of *Lactobacillus gasseri*, *Bacteroides fragilis*, *Faecalibacterium prausnitzii*, *Bacteroides ovatis*, *Shigella*, *Bacteroides dorei*, *Escherichia/Shigella*, *Pseudomons*, *Clostridium maritumum*, *Clostridium bartletii*, *Clostridium romboutsii*, and *Clostridium disporicum*.

In specific cases, when an individual is identified as having or being at risk for recurrent *C. difficile* infection, the individual is treated.

In some embodiments, when the individual has reduced levels of *Lactobacillus gasseri* compared to a control or healthy individual, the individual has or is at risk for having recurrent *C. difficile* infection.

In some embodiments, when the individual has reduced levels of *Bacteroides fragilis* compared to a control or healthy individual, the individual has or is at risk for having recurrent *C. difficile* infection.

In some embodiments, when the individual has reduced levels of *Faecalibacterium prausnitzil* compared to a control or healthy individual, the individual has or is at risk for having recurrent *C. difficile* infection.

In some embodiments, when the individual has reduced levels of *Bacteroides ovatis* compared to a control or healthy individual, the individual has or is at risk for having recurrent *C. difficile* infection.

In some embodiments, when the individual has reduced levels of *Bacteroides dorei* compared to a control or healthy individual, the individual has or is at risk for having recurrent *C. difficile* infection.

In some embodiments, when the individual has increased levels of *Clostridium maritumum*, *Clostridium ruminatium* and/or *Clostridium romboutsii* compared to a control or healthy individual, the individual has or is at risk for having recurrent *C. difficile* infection.

In some embodiments, when the individual has increased levels of *Clostridium bartletii* compared to a control or healthy individual, the individual has or is at risk for having recurrent *C. difficile* infection.

In some embodiments, when the individual has increased levels of *Clostridium disporicum* compared to a control or healthy individual, the individual has or is at risk for having recurrent *C. difficile* infection.

In particular embodiments, the sample is a stool sample.

In certain embodiments, there is a method of treating an individual having or at risk of having recurrent pathogenic *Clostridium* infection, comprising the step of administering a *Clostridium* treatment to the individual when there are alterations in gut microflora and the alterations are determined by nucleic acid analysis of a sample from the individual. The *Clostridium* may be *Clostridium difficile*, *Clostridium perfingens*, *Clostridum botulinum*, *Clostridium maritumum*, *Clostridium ruminatium*, *Clostridium romboutsii*, *Clostridium bartletii*, *Clostridium disporicum* or a mixture thereof. In specific embodiments, the nucleic acid is DNA that encodes 16S rRNA or that is reverse transcribed from 16S rRNA. In a specific embodiment, the microflora comprises bacteria selected from the group consisting of *Lactobacillus gasseri*, *Bacteroides fragilis*, *Faecalibacterium prausnitzii*, *Bacteroides ovatis*, *Shigella*, *Bacteroides dorei*, *Escherichia/Shigella*, *Pseudomonas*, *Clostridium maritumum*, *Clostridium ruminatium*, *Clostridium romboutsii*, *Clostridium bartletii*, *Clostridium disporicum*, and a combination thereof.

In certain aspects, the presence and/or level of a family member of a particular bacteria from the gut microflora is assayed for to determine if an individual will have, has, or is at risk for having recurrent CDI. Genera within the Clostridiaceae family includes *Acetanaerobacterium*; *Acetivibrio*; *Acidaminobacter*; *Alkaliphilus*; *Anaerobacter*; *Anaerotruncus*; *Anoxynatronum*; *Bryantella*; *Butyricicoccus*; *Caldanaerocella*; *Caloramator*; *Caloranaerobacter*; *Caminicella*; *Candidatus Arthromitus*; *Clostridium* (including *Clostridium perfingens*, *Clostridum botulinum*, or a mixture thereof); *Coprobacillus*; *Dorea*; *Ethanologenbacterium*; *Faecalibacterium*; *Garciella*; *Guggenheimella*; *Hespellia*; *Linmingia*; *Natronincola*; *Oxobacter*; *Parasporobacterium*; *Sarcina*; *Soehngenia*; *Sporobacter*; *Subdoligranulum*; *Tepidibacter*; *Tepidimicrobium*; *Thermobrachium*; *Thermohalobacter*; and *Tindallia*. Genera within the Peptostreptococcaceae family includes *Clostridium* (including *Clostridium difficile*); *Filifactor*; *Finegoldia*; *Fusibacter*; *Helcococcus*; *Peptostreptococcus*; and *Tissierella*.

In certain embodiments, there is a method of treating an individual having or at risk of having recurrent pathogenic *Clostridium difficile* infection, comprising the step of administering a *Clostridium* treatment to the individual when analysis of 16S rRNA level of bacteria from a stool sample from the individual shows reduced levels of *Lactobacillus* gasseri, Bacteroides fragilis, Faecalibacterium prausnitzil, Bacteroides ovatis, Shigella, Bacteroides dorei, Enterococcus, and/or Pseudomonas compared to a control or healthy individual.

In certain embodiments, there is a method of treating an individual having or at risk of having recurrent pathogenic Clostridium difficile infection, comprising the step of administering a Clostridium treatment to the individual when analysis of 16S rRNA level of bacteria from a stool sample from the individual shows increased levels of bacteria belonging to the families Clostridiaceae and Peptostreptococcaceae, including, Clostridium maritumum, Clostridium romboutsii, Clostridium bartletii, and/or Clostridium disporicum compared to a control or healthy individual.

In some cases, when an individual has increased levels of Pseudomonas, Enterococcus, Shigella, and/or Escherichia compared to a healthy or CDI patient, the individual has or is at risk of CDI misdiagnosis. Embodiments of the disclosure includes methods of avoiding a misdiagnosis of CDI in an individual, wherein when individual has increased levels of Pseudomonas, Enterococcus, Shigella, and/or Escherichia compared to a healthy or CDI patient, the individual has or is at risk of CDI misdiagnosis.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention. Other embodiments of the invention are discussed throughout this application. It is contemplated that any embodiment discussed herein can be implemented with respect to any method or composition of the invention, and vice versa. Furthermore, compositions and kits of the invention can be used to achieve methods of the invention.

BRIEF DESCRIPTION OF THE DRAWINGS

For a more complete understanding of the present invention, reference is now made to the following descriptions taken in conjunction with the accompanying drawing, in which.

DETAILED DESCRIPTION

Figure 1:
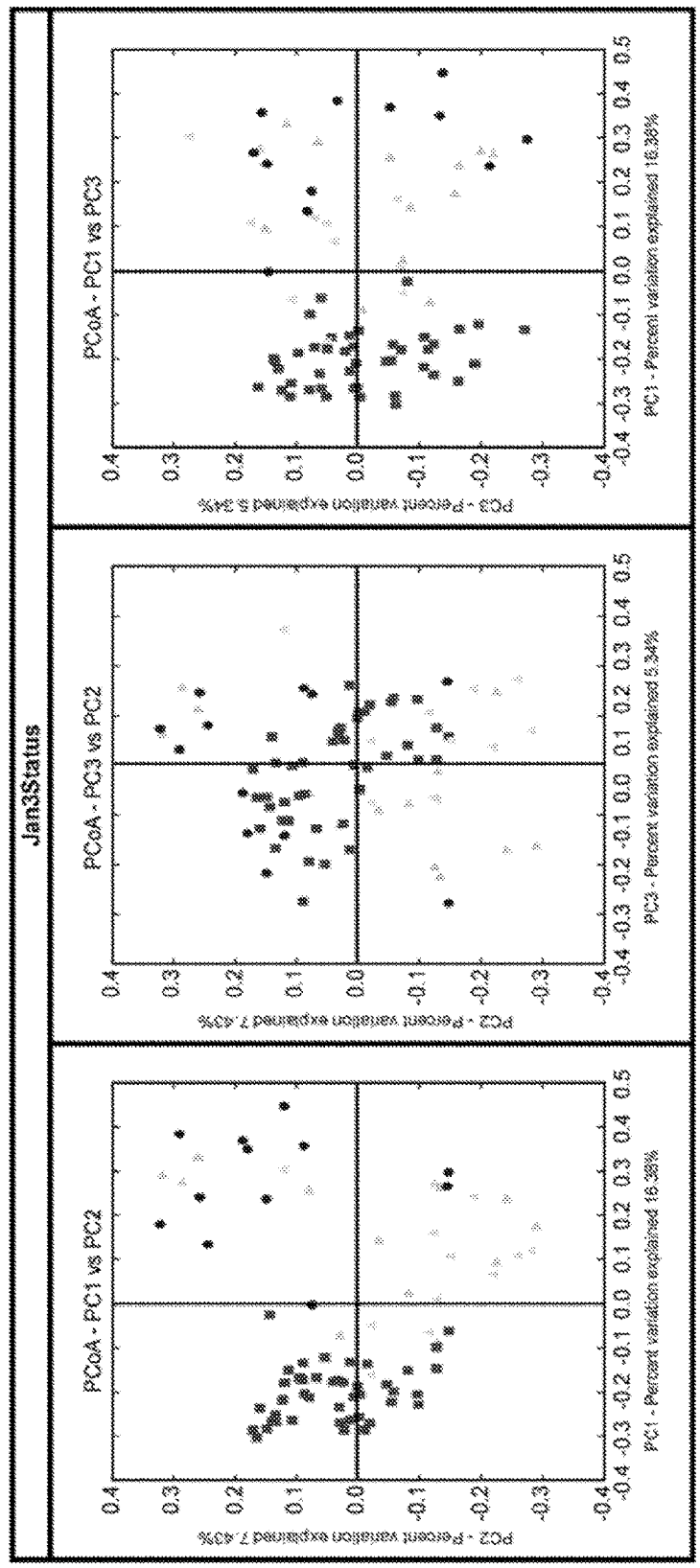
FIG. 1 provides principle coordinates analysis of unweighted Unifrac distances. Gut communities, characterized by 16S rRNA gene sequencing, are shown, colored by *C. difficle* infection status. Squares are Human Microbiome Project (HMP; an NIH-funded initiative to characterize the bacteria associated with the healthy (human) adult body. This data is publically available and was used to provide a reference control) healthy control; triangles are non-recurrent CDI patients via 16S, and circles are recurrent CDI patients-via 16S.

PCT Application Serial No. PCT/US12/64218, filed Nov. 8, 2012, and entitled "Methods and Uses for Metabolic Profiling for *Clostridium difficile* Infection", is incorporated by reference herein in its entirety.

I. Exemplary Definitions

The use of the term "detecting" refers to determining the presence, absence, or amount of an analyte in a sample, and can include quantifying the amount of the analyte in a sample.

As used herein "diagnostic" refers to identifying the presence or nature of a pathologic condition. Diagnostic methods differ in their specificity and sensitivity. While a particular diagnostic method may not provide a definitive diagnosis of a condition, it suffices if the method provides a positive indication that aids in diagnosis.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

II. General Embodiments

Anaerobic bacteria, i.e., those that grow in oxygen-depleted environments, such as the intestines of a mammal, are important to the well-being of the mammal. Gram-positive anaerobes, such as *Lactobacilli, Bifidobacteria*, and *Eubacteria*, and Gram-negative anaerobes, such as *Bacteroides*, represent "good" intestinal organisms, whereas the Gram-positive anaerobe *Clostridium difficile* is a pathogenic bacterium. *Clostridium difficile* has been increasingly associated with disease in human patients, ironically often as a result of treatment with certain antibiotic drugs. The most common disease is referred to as *C. difficile*-associated diarrhea (CDAD). The inventors describe the use of analysis of the nucleic acids from a stool sample to provide a treatment and diagnostic approach for identifying and classifying *C. difficile* infection (CDI) in a subject.

Certain embodiments include the identification and/or categorization of microflora profiles in stool samples and identification of certain aspects of the profile as biomarkers of pathology, clinical phenotype, activity, and/or treatment. The inventors have identified certain microflora populations in subjects with pathological conditions, such as gastrointestinal conditions or symptoms thereof. In certain aspects, the subjects present with symptomatic colonic inflammation or microbial infection. In certain aspects the levels of biomarkers measured are used for analysis of disease classification, diagnosis, or prognosis.

Based on recent findings, the concept is that the nucleic acid analysis can be used to predict disease type and progression in subjects, such as CDI patients. The concept is based on the rationale that gut microbe composition (and dietary or prebiotic factors) are important determinants in whether subjects have certain conditions, are susceptible to certain conditions, or are susceptible to relapse of such a condition.

Analysis of the microflora of the intestinal tract has identified highly significant differences in bacterial population profiles that have enabled the inventors to positively categorize individuals with *C. difficile* infection from other cases of diarrhea (including antibiotic-associated diarrhea, for example) with a high degree of confidence. Alterations in levels of certain bacteria were evident.

III. *C. difficile* Infection

The disclosure concerns methods of treatment for recurrent *C. difficile* infection (CDI) or avoiding certain treatments and/or initiating alternative treatments when the individual lacks pathogenic CDI.

CDI can range from mild to fatal, and symptoms of lesser cases include watery diarrhea, three or more times a day for several days, with abdominal pain or tenderness. An individual with a mild case, moderate case, or a severe case of CDI may be subjected to methods of the invention. Symptoms of more severe CDI include: watery diarrhea (for example, up to 15 times each day); severe abdominal pain; loss of appetite; fever; blood or pus in the stool; and/or weight loss. Certain CDI can lead to a hole in the intestines, which can be lethal if not treated immediately.

IV. Sample Preparation

In certain aspects, a biological sample can be processed to make it compatible with various analysis techniques to be employed in the detection and measurement of biomarkers in the sample. Processing can range from as little as no further processing to more complex methods, all of which are routine in the art.

Samples may be processed in one or more ways to obtain nucleic acid. Nucleic acid may be extracted from samples, including stool samples. In exemplary cases, nucleic acids may be extracted using an extraction kit (which may be called an isolation kit). In specific embodiments, materials and methods are employed to isolate microbial genomic DNA from any type of sample, as well as fecal, stool and biosolid samples. Isolation procedures include removal of inhibitors for analysis of nucleic acid (such as PCR, QPCR and next generation sequencing), including PCR inhibitors. An example of a kit includes MoBio PowerSoil® DNA extraction kits, employing HMP modifications to the manufacturer's protocol.

The sample for testing may be obtained by the individual by routine methods in the art. Examples include rectal swabs, colonic biopsy, colonic washout or irrigation.

V. Additional Embodiments for *C. difficile* Identification

Embodiments of the invention include identification of *C. difficile* by assaying for one or more nucleic acids from an organism in question. In specific embodiments, the nucleic acids that are assayed for comprise the DNA that encodes 16S rRNA or one or more other targets specific to *C. difficile*.

In additional embodiments to assaying for nucleic acid that is specific for *C. difficile* (in specific embodiments for a pathogenic strain of *C. difficile*), there are some embodiments of the invention that utilize one or more assays for identification of *C. difficile*. Examples include cytotoxin assay (which may include ELISA, for example), GDH assay, bacterial culture assay, immunocytotoxicity assay, and/or presence of diarrhea.

A common standard assay for CDI employs stool specimens that are serially diluted and exposed to cells in culture in the presence and absence of specific anti-*C. difficile* toxin A and B neutralizing antibodies. Specificity is determined by cytotoxicity titer and inhibition by antitoxin.

VI. Methods of Treating CDI

*C. difficile* treatment is complicated by the fact that antibiotics can trigger *C. difficile*-associated disease. Nevertheless, antibiotics are the primary treatment option at present.

In some aspects, antibiotics least likely to cause *C. difficile* associated disease are vancomycin and metronidazole. Vancomycin resistance evolving in other microorganisms is a cause for concern in using this antibiotic for treatment, as it is the only effective treatment for infection with other microorganisms (Gerding, Curr. Top. Microbiol. Immunol. 250:127-39, 2000).

In embodiments of the invention, Fidaxomicin is used in the treatment of CDI. Other or additional antibiotics for treating *C. difficile* include metronidazole, vancomycin, fidaxomicin, rifampicin, rifaximin, nitazoxanide or rifabutin used singly or in combinations. Probiotic therapies include administering non-pathogenic microorganisms that compete for niches with the pathogenic bacteria. For example, treatment of *C. difficile* with a combination of vancomycin and *Saccharomyces boulardii* has been reported (McFarland et al., JAMA., 271(24):1913-8, 1994. Erratum in: JAMA, 272(7):518, 1994). A probiotic composition can comprise a microorganism selected from *Lactobacilli, Bifidobacteria, E coli, Eubacteria, Saccharomyces* species, *Enterococci, Bacteroides* or non-pathogenic *Clostridia*, e.g. *Clostridium butyricum* and non-pathogenic *Clostridium difficile*. As will be appreciated by one of skilled in the art, other suitable probiotics known in the art may also be used.

Other therapies include administering therapeutic antibodies. Therapeutic antibodies include those antibodies that bind and inhibit *C. difficile* or *C. difficile* toxins, the inhibition of which provides a therapeutic benefit. The network visualization and quantitative analysis of the CDI metabolome has identified a novel nutraceutical strategy in CDI, phytic acid supplementation. Phytic acid (known as inositol hexakisphosphate (IP6), or phytate when in salt form) is the principal storage form of phosphorus in many plant tissues, especially bran and seeds. Phytate is not digestible to humans or non-ruminant animals. Catabolites of phytic acid are called lower inositol polyphosphates. Examples are inositol penta-(IP5), tetra-(IP4), and triphosphate (IP3). In certain aspects phytic acid supplementation can include administering phytic acid or other inositol polyphosphates or their derivatives. Phytic acid supplementation is useful as treatment for *C. difficile* infection, in certain embodiments.

Two or more therapies for infection may be employed, in certain embodiments of the invention.

In some cases when the CDI is completely refractory to treatment, the individual may be given a Fecal (faecal) microbiota transplantation (FMT), also known as a stool transplant.

VII. Pharmaceutical Preparations

Pharmaceutical compositions of the present invention comprise an effective amount of one or more CDI treatment(s) dissolved or dispersed in a pharmaceutically acceptable carrier. Examples of one or more CDI treatments includes metronidazole, vancomycin, fidaxomicin, rifampicin, rifaximin, nitazoxanide or rifabutin, probiotic therapies, and/or therapeutic antibodies.

The phrases "pharmaceutical or pharmacologically acceptable" refers to molecular entities and compositions that do not produce an adverse, allergic or other untoward reaction when administered to an animal, such as, for example, domestic animals or livestock or a human, as appropriate. The preparation of an pharmaceutical composition that contains at least one composition will be known to those of skill in the art in light of the present disclosure, as exemplified by Remington: The Science and Practice of Pharmacy, 21$^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The composition may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The composition may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include composition, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the composition may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In preferred embodiments of the present invention, the compositions are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, trehalose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, composition may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,7537,514, 6,613,308, 5,466,468, 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the active compound composition may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

VIII. Kits of the Invention

Any of the compositions described herein may be comprised in a kit. In a non-limiting example, one or more reagents to analyze nucleic acid and/or one or more CDI therapies may be comprised in a kit. The kits will comprise any of its components in suitable container means.

The kits may comprise a suitably aliquoted reagent or therapeutic compositions of the present invention. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing any composition and any reagent containers in close confinement for commercial sale. Such containers may include injection or blow-molded plastic containers into which the desired vials are retained.

However, the components of the kit may be provided as dried powder(s). When reagents and/or components are provided as a dry powder, the powder can be reconstituted by the addition of a suitable solvent. It is envisioned that the solvent may also be provided in another container means.

Irrespective of the number and/or type of containers, the kits of the invention may also comprise, and/or be packaged with, an instrument for assisting with the injection/administration and/or placement of the therapeutic composition within the body of an animal. Such an instrument may be a syringe, pipette, forceps, and/or any such medically approved delivery vehicle. Other compositions that may be included in the kit are those that are useful to obtain a sample, such as a stool sample.

In certain embodiments of the invention, the kit comprises one or more reagents or compositions that are utilized in analysis of nucleic acid, including from a sample from an individual. The kit may also include reagents for initial purification of nucleic acid from a raw sample. Exemplary reagents for nucleic acid analysis includes deoxyribonucleotides, buffers, salts, polymerase (include thermally active polymerase for PCR), and/or one or more primers that target at least one region of a nucleic acid that allows specific identification of an organism. In some embodiments, the target is highly conserved within a species of an organism, such as 16S rRNA. In certain embodiments, the target is specific to the organism but is not 16S rRNA or any housekeeping gene, for example.

IX. Analysis of Nucleic Acids and Nucleic Acid Detection

Nucleic acids from the samples may be detected by any suitable method, including one or more of the following exemplary methods. In specific embodiments, 16S rRNA, the DNA that encodes it, or DNA that is reverse transcribed from it, are assayed for in methods of the invention.

1. Hybridization

The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, site-directed mutagenesis, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

2. Amplification of Nucleic Acids

Nucleic acids used as a template for amplification may be isolated from cells, tissues or other samples according to standard methodologies (Sambrook et al., 1989). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to 16S RNA (for example) are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 1989). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR oligonucleotide ligase assy (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

3. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 1989). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

4. Other Assays

Other methods for genetic screening may be used within the scope of the present invention, for example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR above), single-strand conformation polymorphism analysis ("SSCP") and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substititution mutations that may be used in the practice of the present invention are disclosed in U.S. Pat. Nos. 5,849,483, 5,851,770, 5,866,337, 5,925,525 and 5,928,870, each of which is incorporated herein by reference in its entirety.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

A Multi-Omics Approach to Understanding the Gut-Microbial Ecology and Mechanisms of Recurrent *Clostridium Difficile* Infection Despite a known correlation between antimicrobial disruption of protective gut microflora and the development of symptoms in infected individuals, there is still a major gap in our understanding of why certain individuals are susceptible to disease recurrence by *C. difficile*. To address this question, the inventors profiled stool microbial community composition and the metabolome from individuals with and without CDI, and found that patients who subsequently develop recurrent disease have significant shifts in microbial populations and biochemical composition. Patients with recurrent disease were identified with decreased abundances of taxa belonging to the families Bacteroidaceae and Prevotellaceae, and increased abundances of taxa belonging to the families Peptostreptococcaceae (including *C. difficile*) and Clostridiaceae. Notably, in patients with recurrent CDI, the Pepostreptococcaceae and Clostridiaceae accounted for ≥40% of all 16S rRNA sequence recovered. Concurrent with changes in microbial community structure, significantly elevated levels of γ-aminobutyric acid (GABA) and precursors of GABA synthesis were also detected. GABA is synthesized by gut bacteria and is a potent amino acid neurotransmitter that has various physiologic effects throughout the body. GABA and its agonists, induce neural modulation as a consequence of their interaction with specific binding sites for each of these classes of neuroactive substances on the GABA receptor complex of postsynaptic neurons. Using agonists and antagonists of the GABA transaminase and receptor respectively, the inventors demonstrate that GABAergic signals directly regulate *C. difficile* neurotoxin activity and cytokine secretion in experimental CDI. In embodiments of the invention these processes contribute to increased CDI severity and recurrence.

The inventors demonstrate that integration of global metabolomics and metagenomics into ecosystem network models provides an organizational and analytical framework for the discovery of new diagnosis and treatment in CDI. At least one significance of this multi-omics approach is the identification of a novel microbe-neuroimmune signaling mechanism in patients with recurrent disease.

Example 2

Community Composition

The exemplary 16S ribosomal RNA gene is taxonomically informative for bacteria and archaea (i.e., the identity of a bacterium or archaeon can be discerned from the specific sequence of the organism's 16S rRNA gene(s). Additionally, the sequence composition of the 16S rRNA gene can be utilized to determine identity at multiple taxonomic levels (i.e., Phylum, Class, Order, Family, Genus, and Species).

Bacterial community composition is commonly characterized by obtaining mixed genomic DNA from a specimen of interest (e.g., stool, soil, dust, water, skin cells). This pool of DNA is amplified using primers that target the 16S rRNA gene, and this pool is then sequenced. The resulting sequence data may be queried (i.e. BLAST) against sequence databases in order to discern identity. Commonly, the sequences clustered into operational taxonomic units (OTUs) before the querying sequence databases (such as NCBI nr, the Ribosomal Database Project, or Greengenes). OTU clustering is performed on the basis of sequence similarity, and it is a computational means of identifying species from large, mixed pools of 16S rRNA gene sequence data.

The present examples concerns demonstration of the populations of microflora in the gut if those with CDI (and those having recurrent CDI) compared to those without CDI. FIG. 1 demonstrates exemplary gut communities by showing principle coordinates analysis of unweighted Unifrac distances. Such results are illustrated by the detection of diagnostic and prognostic *C. difficle* disease profiles via 16S rRNA gene sequencing. Squares are (Human Microbiome Project) HMP healthy control; circles are recurrent CDI-patients via 16S, and triangles are nonrecurrent CDI patients via 16S.

Figure 2:
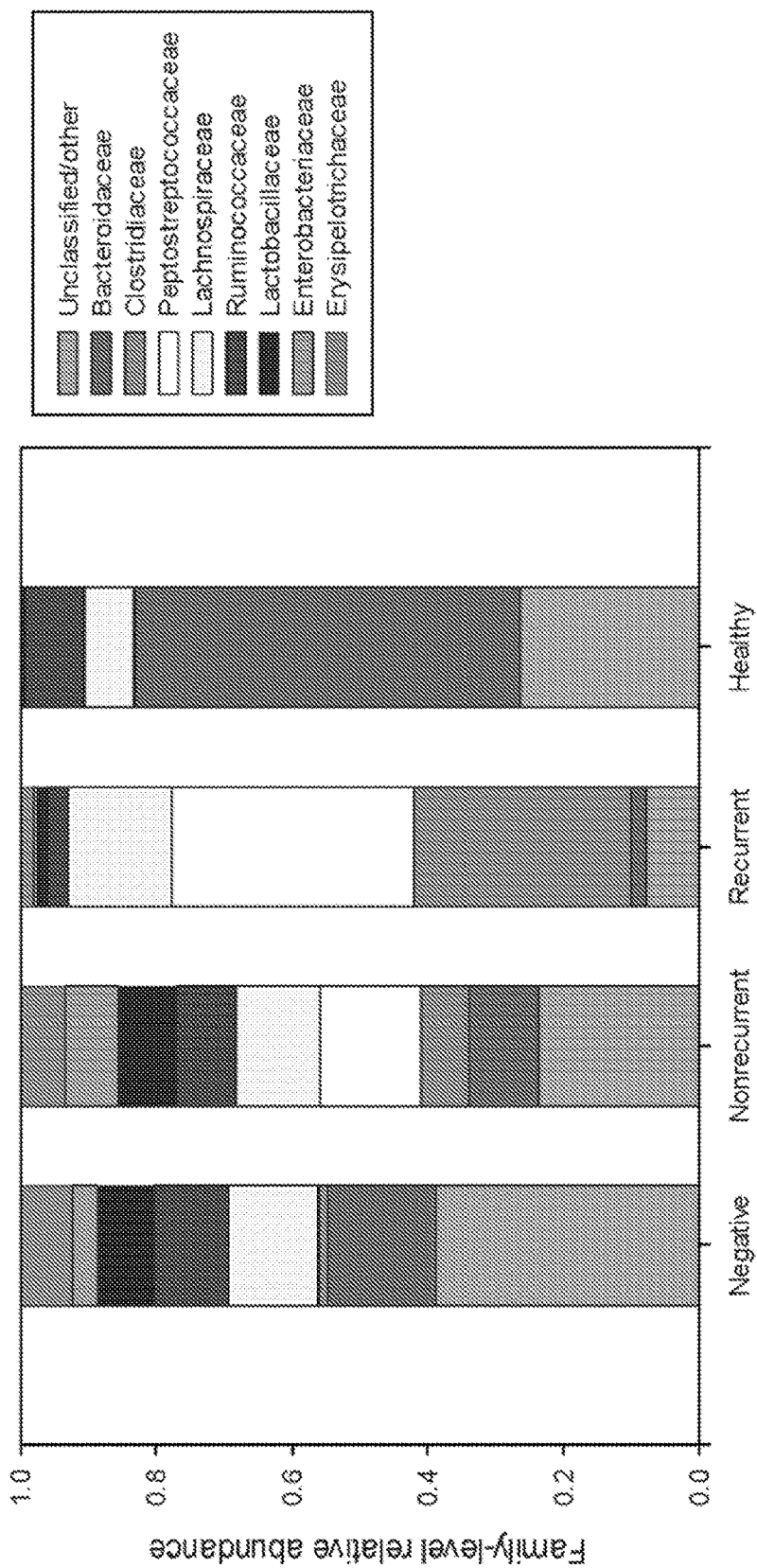
FIG. 2 shows distribution of bacterial families relative to CDI status. Negative: non-CDI cases of antibiotic-associated diarrhea; Nonrecurrent: cases of primary CDI only; Recurrent: CDI individuals who relapse within 6 weeks of initial infection; Healthy: Houston-based participants (healthy adults) from the Human Microbiome Project.

FIG. 2 shows distribution of bacterial families relative to CDI status.

Example 3

Predicting the Likelihood of Recurrence of CDI

In embodiments of the invention, multiple taxa contribute to the signature of recurrent CDI.

Figure 3:
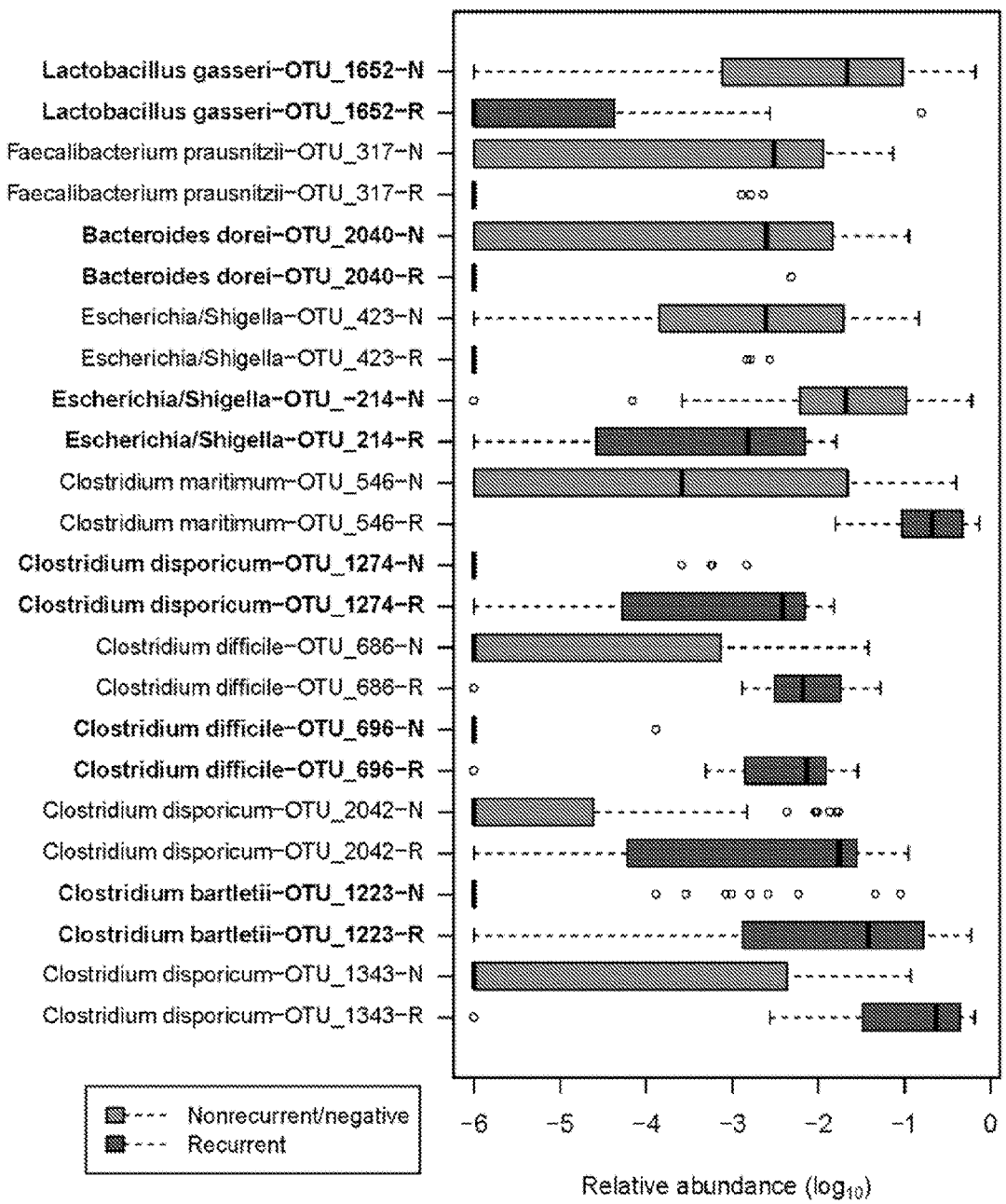
FIG. 3 demonstrates OTUs (operational taxonomic units, a numerical approach to clustering sequence data into species) identified by supervised learning as having discriminating and/or predictive power with respect to the classification of recurrent CDI. Although *C. difficile* is identified as a part of the recurrent CDI "fingerprint", multiple other *Clostridium* species are enriched significantly in, and contribute to the signature of, recurrent CDI. N refers to CDI negative and non-recurrent individuals, and R refers to recurrent CDI individuals.

The 16S-based signature of recurrent CDI is apparent at multiple taxonomic levels. It is apparent at the operational taxonomic units (OTU) (i.e., numerical "species") level, as illustrated by the red/gray bar graph included in FIG. 3. This exemplary signature includes significantly reduced abundances of *Lactobacillus gasseri* and *Faecalibacterium prausntizii*, as well as increased abundances of *C. difficile, C. maritimum/C. romboutsii/C. ruminatium, C. disporicum*, and *C. bartletii*. The predictive accuracy of this signature is ~88% (i.e. error rate of 12%).

This signature may also be detected at the family level, in certain embodiments, and it is based on the relative abundance of two bacterial families (i.e. the Clostridiaceae and the Peptostreptococcaceae). Subjects with recurrent CDI are characterized by stool bacterial communities whose 16S rRNA gene profiles contain 40% or more of bacteria belonging to the families Clostridiaceae and Peptostreptococcaceae (i.e. the sum of the relative abundances of these two bacterial families is ≥40%). Genera within the Clostridiaceae family includes *Acetanaerobacterium; Acetivibrio; Acidaminobacter; Alkaliphilus; Anaerobacter; Anaerotruncus; Anoxynatronum; Bryantella; Butyricicoccus; Caldanaerocella; Caloramator; Caloranaerobacter; Caminicella; Candidatus Arthromitus; Clostridium; Coprobacillus; Dorea; Ethanologenbacterium; Faecalibacterium; Garciella; Guggenheimella; Hespellia; Linmingia; Natronincola; Oxobacter; Parasporobacterium; Sarcina; Soehngenia; Sporobacter; Subdoligranulum; Tepidibacter; Tepidimicrobium; Thermobrachium; Thermohalobacter*; and *Tindallia*. Genera within the Peptostreptococcaceae family includes *Filifactor; Clostridium, Finegoldia; Fusibacter; Helcococcus; Peptostreptococcus*; and *Tissierella*.

Table 1. Performance of classification model based upon 16S rRNA gene features in subjects with recurrent CDI, non-recurrent CDI, and subjects from the Human Microbiome Project. Subjects misclassified by the classification rule (sum of the relative abundances of Peptostreptococcaceae and Clostridiaceae >40% of the total community) were also apparent outliers in our metabolomics-based classification of subjects.

| Subject type | Predicted classification | | Error rate |
| --- | --- | --- | --- |
| | Negative/Nonrecurrent | Recurrent | |
| Negative/Nonrecurrent | 4 | 75 | 5% |
| Recurrent | 8 | 13 | 38% |
| | | | 12% |

TABLE 2

Correlation of OTUs with metabolites that differ significantly between subjects with recurrent CDI and those with non-recurrent CDI (partial list of >80 metabolites).

| OTU ID | Metabolite (predictive rank) | Correlation (r) | p-value |
| --- | --- | --- | --- |
| Clostridium disporicum (OTU 1274) | Beta-hydroxyisovalerate (5) | 0.669137 | 0.000255 |
| Unclassified Ruminococcaceae (OTU 664) | X-11877 (7) | 0.710896 | 6.81E−05 |
| Acinetobacter sp. (OTU 1494) | Methionylisoleucine (8) | 0.684412 | 0.000161 |
| Acinetobacter sp (OTU 1885) | Methionylisoleucine (8) | 0.679925 | 0.000185 |
| Clostridium symbiosum (OTU 896) | Deoxychoate (9) | 0.677014 | 0.000202 |
| Ruminococcus sp. (OTU 738) | Pyridoxate (14) | 0.854419 | 5.48E−08 |
| Unclassified Ruminococcaceae (OTU 209) | Pyridoxate (14) | 0.863875 | 2.66E−08 |
| Unclassified Ruminococcaceae (OTU 664) | Pyridoxate (14) | 0.739764 | 2.38E−05 |
| Clostridium sp. (OTU 815) | N-acetylglycine (16) | 0.799928 | 1.60E−06 |

Thus, in embodiments of the invention, decreased abundances of taxa belonging to the families Bacteroidaceae and Prevotellaceae, and/or increased abundances of taxa belonging to the families Peptostreptococcaceae and Clostridiaceae were identified in CDI recurrence.

Development of 16S (and in some embodiments also metabolite) biomarkers of CDI recurrence will address a significant unmet medical need by providing medical providers with valuable information that improves therapeutic decision-making and patient management.

Example 4

PCR Misdiagnosis of *C. Difficile*

Present methods in the art for diagnosis of CDI result in an unacceptable level of misdiagnosis. Those methods often include PCR (including real-time PCR) at least in part, and the present example concerns misdiagnosis of *C. difficile* by prior methods in the art. PCR methods may be too sensitive for diagnosis of CDI and may be measuring *C. difficile* that is not clinically relevant. Such misdiagnosis leads to treatment for CDI that can be harmful to the individual, depending on their gut microflora.

Thus, in particular aspects of the disclosure, method steps do not include PCR in the assay determination step itself or PCR is not the sole assay method employed. For example, PCR may be utilized for amplification of subpar levels of nucleic acid, but other steps are utilized for subsequent manipulation or analysis of the PCR product (such as sequencing). Particular embodiments employ sequencing in the method steps for analysis of bacterial community composition, including 16S rRNA gene sequencing via Sanger sequencing or "next-generation" methods (e.g., 454, Illumina, IonTorrent, PacBio), deep sequencing, whole genome sequencing, or shotgun metagenome sequencing, and phylogenetic microarrays (e.g., Phylochip).

Figure 4:
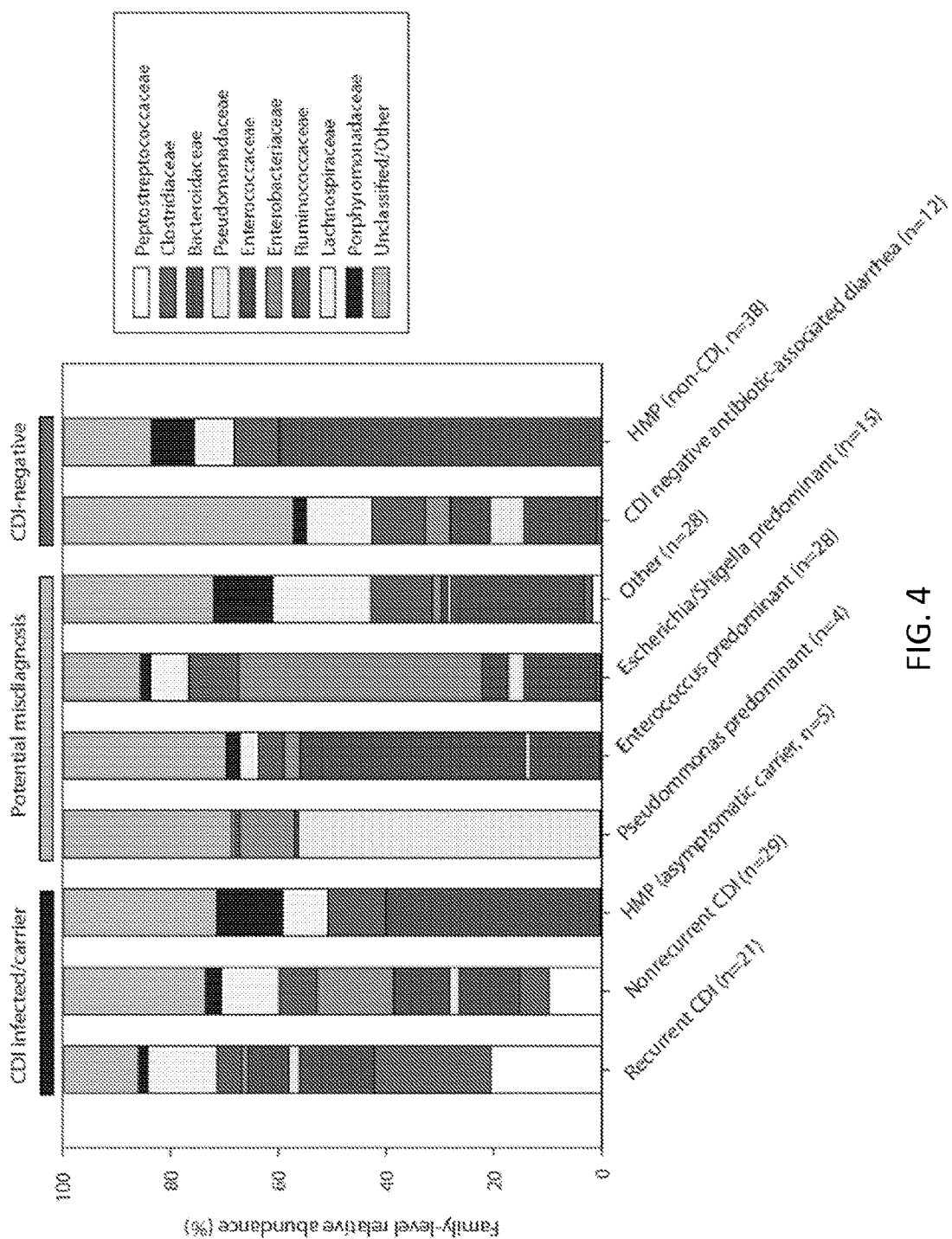
FIG. 4 illustrates the distribution of bacterial families relative to CDI status including potentially misdiagnosed cases.

FIG. 4 illustrates the distribution of bacterial families relative to CDI status. Subjects under the potential misdiagnosis heading are those who were diagnosed as *C. difficile*-positive but did not contain sequences resembling *C. difficile* in their 16S rRNA gene profiles. Many of these potential misdiagnoses, however, did show enrichment of other potentially problematic or pathogenic taxa in their profiles. Key taxa are highlighted below. Recurrent: CDI individuals who relapse within 6 weeks of initial infection; Nonrecurrent: cases of CDI that did not result in subsequent relapse within 6 weeks of initial diagnosis; HMP asymptomatic carrier: healthy Houston-based subjects from the Human Microbiome Project who are asymptomatic carriers of *C. difficile*; Pseudomonas predominant: potentially misdiagnosed subjects whose profiles showed an enrichment of sequences belonging to the genus *Pseudomonas*; Enterococcus predominant: potentially misdiagnosed subjects whose profiles showed an enrichment of sequences belonging to the genus *Enterococcus*; *Escherichia/Shigella* predominant: potentially misdiagnosed subjects whose profiles showed an enrichment of sequences belonging to the genera *Escherichia/Shigella*. Other: potentially misdiagnosed subjects whose profiles did not show a specific enrichment of *Pseudomonas, Enterococcus,* or *Escherichia/Shigella*. CDI negative: non-CDI cases of antibiotic-associated diarrhea; Healthy: Houston-based participants (healthy adults) from the Human Microbiome Project.

In particular, FIG. 4 illustrates information from 137 suspected-CDI subjects and 43 healthy HMP control subjects (38 of whom did not have *C. difficile* in their profiles, 5 asymptomatic carriers of *C. difficile*). Of the 137 suspected-CDI cases, 75 appear to be misdiagnosed (i.e., are false positives by 16S sequencing). This represents a misdiagnosis rate of 54.7%.

A classification table is disclosed elsewhere herein where re-analysis of the classification error rates has been performed using a classification rule that is defined by the combined relative abundances of 16S rRNA gene sequences belonging to the families Peptostreptococcaeae and Clostridiaceae (if % Peptostreptococcaceae+% Clostridiaceae>40%, then is the patient likely to experience recurrent-CDI). If the Human Microbiome Project (HMP), CDI-negative, and CDI-nonrecurrent individuals are represented as one category and CDI-recurrent as another, the classification rule produces an overall error rate of 12%.

The within group misclassifications are as follows:

CDI-Recurrent: 62% correct; 38% misclassified (this equates to 13 of 21 subjects being correctly classified.)

Non-CDI: 95% correct: 5% misclassified (this equates to 75 of 79 subjects being correctly classified.)

If one limits this to suspected CDI cases only (non-CDI=negative and nonrecurrent), then the rule yields a 24% error rate.

CDI-Recurrent: 62% correct; 38% misclassified (This equates to 13 of 21 subjects being correctly classified.)

Non-CDI: 86% correct: 14% misclassified (This equates to 25 of 29 subjects being correctly classified.)

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of identifying and treating an individual having or at risk of having recurrent pathogenic *Clostridium difficile* infection, comprising:
    obtaining a sample from the individual, wherein the sample is a stool sample, rectal swab, colon biopsy, colonic wash out, or colonic irrigation;
    performing nucleic acid analysis on the sample to detect an amount of *Lactobacillus gasseri, Bacteroides fragilis, Faecalibacterium prausnitzil, Bacteroides ovatis,* and *Bacteroides dorei* present in the sample;
    identifying the individual as having or at risk of having recurrent pathogenic *Clostridium difficile* infection when the individual has reduced levels of *Lactobacillus gasseri, Bacteroides fragilis, Faecalibacterium prausnitzil, Bacteroides ovatis,* and *Bacteroides dorei* compared to a control subject or an individual not infected with *Clostridium difricile*; and
    administering a *Clostridium difficile* treatment to the individual when the individual is identified as having reduced levels of *Lactobacillus gasseri, Bacteroides fragilis, Faecalibacterium prausnitzil, Bacteroides ovatis,* and *Bacteroides dorei*, compared to the control or the individual not infected with *Clostridium difficile*.

2. The method of claim 1, wherein the nucleic acid is analyzed by polymerase chain reaction, sequencing, isothermal amplification, bioinformatics, or a combination thereof.

3. The method of claim 1, wherein the nucleic acid encodes 16S rRNA or is reverse transcribed from 16S rRNA.

4. The method of claim 1, further comprising the step of analyzing the sample for one or more toxins from *Clostridium*.

5. The method of claim 1, further comprising the step of analyzing the sample for one or more metabolites.

6. The method of claim 1, further comprising the step of extracting DNA from the sample.

7. The method of claim 1, wherein the nucleic acid is DNA that encodes 16S rRNA or that is reverse transcribed from 16S rRNA.

8. A method of identifying and treating an individual having or at risk of having recurrent pathogenic *Clostridium difficile* infection, comprising:
    obtaining a sample from the individual, wherein the sample is a stool sample, rectal swab, colon biopsy, colonic wash out, or colonic irrigation;
    performing nucleic acid analysis on the sample to detect an amount of *Clostridium maritimum, Clostridium romboutsii, Clostridium ruminatium, Clostridium bartletii,* and *Clostridium disporicum* present in the sample;
    identifying the individual as having or at risk of having recurrent pathogenic *Clostridium difficile* infection when the individual has increased levels of *Clostridium maritimum, Clostridium romboutsii, Clostridium ruminatium, Clostridium bartletii,* and *Clostridium disporicum* compared to a control subject or an individual not infected with *Clostridium difficile*; and
    administering a *Clostridium difficile* treatment to the individual when the individual is identified as having increased levels of *Clostridium maritimum, Clostridium romboutsii, Clostridium ruminatium, Clostridium bartletii,* and *Clostridium disporicum*, compared to the control or the individual not infected with *Clostridium difficile*.

9. The method of claim 8, wherein the nucleic acid is analyzed by polymerase chain reaction, sequencing, isothermal amplification, bioinformatics, or a combination thereof.

10. The method of claim 8, wherein the nucleic acid encodes 16S rRNA or is reverse transcribed from 16S rRNA.

11. The method of claim 8, further comprising the step of analyzing the sample for one or more toxins from *Clostridium*.

12. The method of claim 8, further comprising the step of analyzing the sample for one or more metabolites.

13. The method of claim 8, further comprising the step of extracting DNA from the sample.

* * * * *